(12) United States Patent
Nishtala et al.

(10) Patent No.: US 7,854,725 B2
(45) Date of Patent: Dec. 21, 2010

(54) LOW PROFILE RETENTION SYSTEM

(75) Inventors: Srinivas Nishtala, Bloomington, IN (US); Linda Elbert, Bloomington, IN (US); D. H. Perkins, Bloomington, IN (US); Stephane Gobron, Gosport, IN (US); Jeffrey Smith, Poland, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 34 days.

(21) Appl. No.: 12/335,172

(22) Filed: Dec. 15, 2008

(65) Prior Publication Data

US 2009/0093770 A1 Apr. 9, 2009

Related U.S. Application Data

(60) Continuation of application No. 10/718,639, filed on Nov. 24, 2003, now Pat. No. 7,481,796, which is a division of application No. 09/870,516, filed on Jun. 1, 2001, now Pat. No. 6,676,640, which is a continuation of application No. 09/177,820, filed on Oct. 23, 1998, now Pat. No. 6,287,281, which is a continuation-in-part of application No. 09/109,101, filed on Jul. 2, 1998, now abandoned.

(51) Int. Cl.
*A61M 5/32* (2006.01)
(52) U.S. Cl. .................................... 604/174
(58) Field of Classification Search ............. 604/174, 604/178, 246, 249, 250, 34, 177, 500, 919, 604/127; 251/4, 7
See application file for complete search history.

(56) References Cited

U.S. PATENT DOCUMENTS

| | | |
|---|---|---|
| 2,234,686 A | 3/1941 | Walter |
| 3,760,811 A | 9/1973 | Andrew |
| 3,783,876 A | 1/1974 | Dye |
| 3,821,957 A | 7/1974 | Riely et al. |
| 3,960,149 A | 6/1976 | Bujan |
| 4,164,943 A | 8/1979 | Hill et al. |
| 4,235,229 A | 11/1980 | Ranford et al. |
| 4,248,229 A | 2/1981 | Miller |
| 4,261,363 A | 4/1981 | Russo |
| 4,498,903 A | 2/1985 | Mathew |
| 4,533,349 A | 8/1985 | Bark |
| 4,579,120 A | 4/1986 | MacGregor |
| 4,615,472 A | 10/1986 | Nash |
| 4,653,719 A | 3/1987 | Cabrera et al. |
| 4,717,385 A | 1/1988 | Cameron et al. |
| 4,774,944 A | 10/1988 | Mischinski |
| 4,826,487 A | 5/1989 | Winter |
| 4,932,943 A | 6/1990 | Nowak |
| 5,007,900 A | 4/1991 | Picha et al. |

(Continued)

*Primary Examiner*—Nicholas D Lucchesi
*Assistant Examiner*—Brooke M Matney
(74) *Attorney, Agent, or Firm*—Kenyon & Kenyon LLP

(57) ABSTRACT

Medical devices for retaining an end of a medical tube. Each of the devices of the present invention comprises a base and at least one tab having a portion that is moveable within the base. The base comprises an upper surface, a lower surface, at least one side cavity for receiving a tab, and an opening transverse to the upper and lower surfaces. To facilitate tube retention, the tube is inserted through the opening in the base and the tab(s) is(are) moved within the cavity(ies) such that a portion of each tab contacts and retains the tube.

18 Claims, 9 Drawing Sheets

U.S. PATENT DOCUMENTS

| | | |
|---|---|---|
| 5,026,352 A | 6/1991 | Anderson |
| 5,069,206 A | 12/1991 | Crosbie |
| 5,084,026 A | 1/1992 | Shapiro |
| 5,098,397 A | 3/1992 | Svensson et al. |
| 5,122,122 A | 6/1992 | Allgood |
| 5,137,519 A | 8/1992 | Littrell et al. |
| 5,146,913 A | 9/1992 | Khorsandian et al. |
| 5,224,935 A | 7/1993 | Hollands |
| 5,226,892 A | 7/1993 | Boswell |
| 5,257,973 A | 11/1993 | Villasuso |
| 5,257,975 A | 11/1993 | Foshee |
| 5,257,978 A * | 11/1993 | Haber et al. ............... 604/250 |
| 5,312,337 A | 5/1994 | Flaherty et al. |
| 5,346,479 A | 9/1994 | Schneider |
| 5,364,367 A | 11/1994 | Banks et al. |
| 5,368,575 A | 11/1994 | Chang |
| 5,395,344 A | 3/1995 | Beisang, III et al. |
| 5,453,098 A | 9/1995 | Botts et al. |
| 5,470,321 A | 11/1995 | Forster et al. |
| 5,540,648 A | 7/1996 | Yoon |
| 5,603,699 A | 2/1997 | Shine |
| 5,616,131 A | 4/1997 | Sauer et al. |
| 5,813,402 A | 9/1998 | Jinotti |

* cited by examiner

LOW PROFILE RETENTION SYSTEM

RELATED APPLICATIONS

This is a continuation of U.S. Ser. No. 10/718,639, filed Nov. 24, 2003 now U.S. Pat. No. 7,481,796, which is a divisional of U.S. Ser. No. 09/870,516 (now U.S. Pat. No. 6,676,640), filed Jun. 1, 2001, which is a continuation of U.S. Ser. No. 09/177,820 (now U.S. Pat. No. 6,287,281), filed Oct. 23, 1998, which is a continuation-in-part of U.S. Ser. No. 09/109,101, filed Jul. 2, 1998 (now abandoned).

FIELD OF THE INVENTION

The present invention relates to medical devices for the retention of flexible tubes such as gastrostomy feeding tubes.

BACKGROUND OF THE INVENTION

Various medical procedures result in the placement of flexible tubes within the body. While the distal end of such tubes remains implanted within the body, the proximal end extends outside of the body and must be retained.

For example, a gastrostomy (i.e., percutaneous endoscopic gastrostomy, surgically placed gastrostomy tube, or laparoscopically placed gastrostomy tube) is performed in order to place a gastrostomy or "feeding" tube into a patient's stomach. The patient is fed directly through the feeding tube via the proximal end of the tube, which extends from the patient's body through a stoma site. This procedure is used for long-term feeding and to retain digestive functions of patients suffering from neurological disease, brain injury, or tumors and/or injuries of the head, neck, or esophagus, who thus have swallowing difficulties but otherwise have functioning gastrointestinal tracts.

Another type of medical tube placed within the body are drainage catheters, which are used in interventional radiology to drain fluids from an organ or body cavity. The proximal end of the catheter extends out of the body and typically has a plastic hub, which is attached and secured to the patient.

The proximal ends of tubes such as gastrostomy tubes and drainage catheters must be retained in a fixed position outside of the body to avoid movement into or out of the body and to provide support for feeding procedures and external manipulation. Furthermore, the ends must be closed to prevent the leakage of body fluids from these tubes. Conventional retention systems use multiple components and are cumbersome to use due to inefficient ergonomics. Moreover, conventional retention systems often do not provide sufficient retention strength.

SUMMARY OF THE INVENTION

The present invention includes medical devices for retaining an end of a medical tube. Each of the devices of the present invention comprises a base and at least one tab having a portion that is moveable within the base. The base comprises an upper surface, a lower surface, at least one side cavity for receiving a tab, and an opening in at least one of the upper and lower surfaces. To facilitate tube retention, the tube is inserted through the opening in the base and the tab(s) is(are) moved within the cavity(ies) such that a portion of each tab contacts and retains the tube.

In one embodiment, the present invention includes a medical device comprising a base and a first tab having a portion that is moveable within the base. The base includes a first locking base feature for engaging the first tab. The upper and lower surfaces of the base define a first side cavity between the upper and lower surfaces. The first tab has a portion that is movable within the first side cavity, a first locking tab feature that is engageable with the first locking base feature, and a first tube compression member extending from the distal end of the first tab. To facilitate tube retention, the tube is inserted through the opening in the base, the first tab is moved within the first side cavity, and the first locking tab feature is engaged with the first locking base feature such that the tab is locked into the base and the first tube compression member contacts the tube.

In another embodiment of the present invention, the base includes a second side cavity between the upper and lower surfaces, and a second locking base feature. In this embodiment, the medical device includes a second tab having a portion that is movable within the second side cavity. The second tab includes a second locking tab feature that is engagable with the second locking base feature, and further includes a second tube compression member extending from the distal end of the second tab. To facilitate tube retention, the tube is inserted through the opening in the base, the first and second tabs are moved within the first and second side cavities, respectively, and the first and second locking tab features are engaged with the first and second locking base features, respectively, such that the tabs are locked into the base and the first and second tube compression members contact the tube.

DETAILED DESCRIPTION

The present invention relates to the retention of flexible plastic tubes at desired locations and orientations in medical applications. The medical devices of the present invention are suitable for use in any application in which a flexible tube extends from the body and must be retained. Such applications include, for example, gastrostomy tubes, jejunostomy tubes, and drainage catheters (e.g., nephrostomy, abscess, urinary, and biliary drainage, and other multipurpose drainage applications). The medical devices of the present invention retain and support the ends of these tubes when protruding from the body. The medical devices of the present invention are low profile and thus easily fit beneath a patient's clothing. Furthermore, the medical devices of the present invention are easy to use and provide high retention strength. A further advantage of the medical devices of the present invention is that they provide a novel and reliable valve and feeding system interface.

Figure 1:
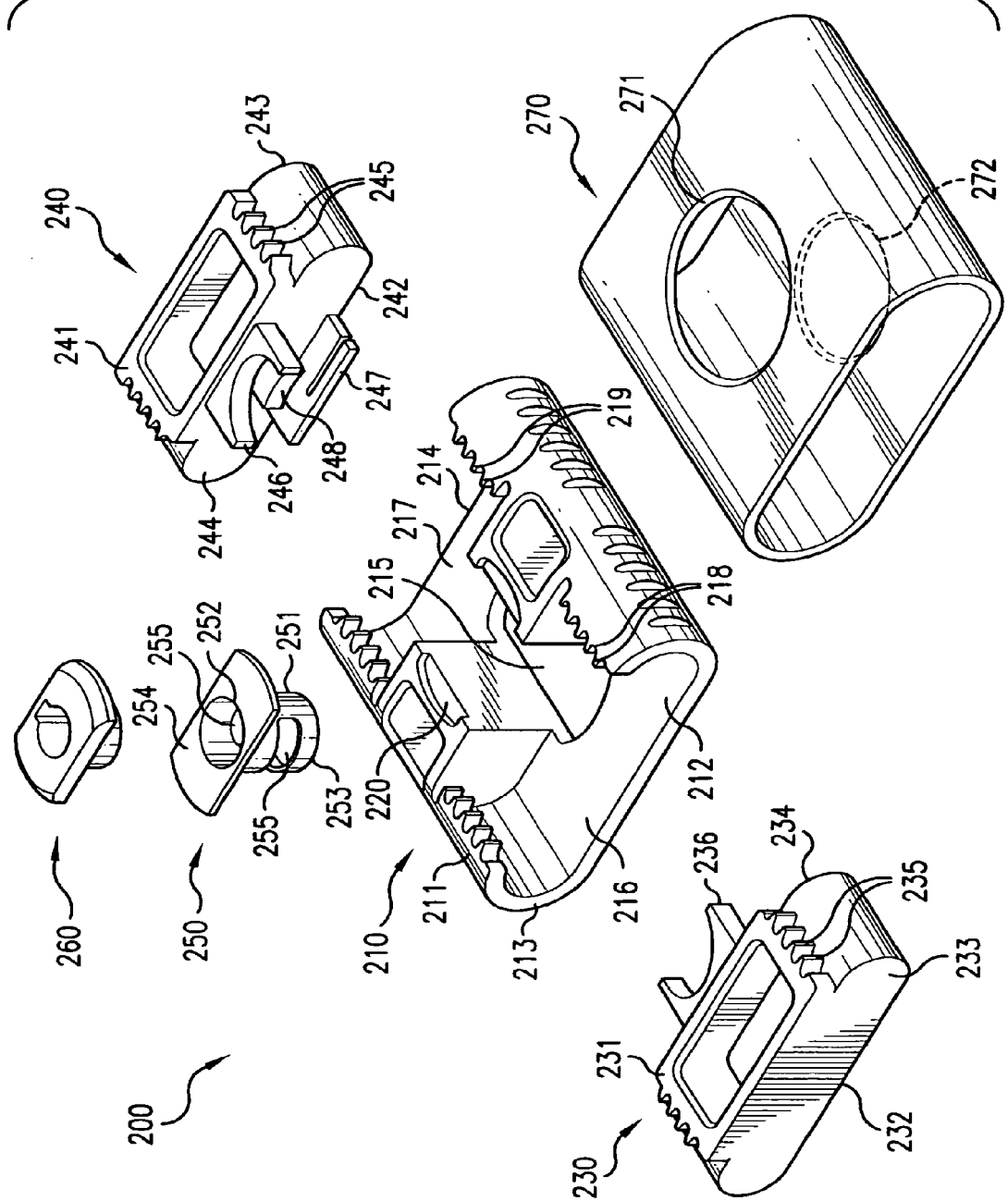
FIG. 1 shows an exploded view of the components of an embodiment of the present invention in which two tabs are used.

One embodiment of the present invention, including its various components, is shown in FIG. 1. The medical device 200 includes a base 210, a first tab 230, a second tab 240 and a stem 250.

The base 210 includes upper and lower surfaces 211, 212, and proximal and distal ends 213, 214. The upper and lower surfaces 211, 212 define an opening 215 for receiving a tube to be retained. The upper and lower surfaces 211, 212 further define a first side cavity 216 and a second side cavity 217. The first side cavity 216 extends from the opening 215 to the proximal end 213. The second side cavity 217 extends from the opening 215 to the distal end 214. In this embodiment, the base 210 includes a plurality of first locking base features 218 in the upper surface 211 between the opening 215 and the proximal end 213. The base 210 further includes a plurality of second locking members 219 in the upper surface 211 between the opening 215 and the distal end 214.

The medical device 200 includes first and second tabs 230, 240, which are substantially identical in structure. The first and second tabs 230, 240 are movable within first and second cavities 216, 217, respectively. The first and second tabs 230, 240 comprise respective upper 231, 241 and lower 232, 242 surfaces. The upper surfaces 231, 241 each have at least one locking tab feature 235, 245 that is (are) engagable with respective locking base features 218, 219. The first and second tabs 230, 240 further comprise tube compression members 236, 246 and window locking members (shown as 248 for the second tab 240) extending from distal ends 234, 244, respectively. The first and second tabs 230, 240 each optionally include respective tube closing members (shown as 247 for the second tab 240). The base 210 and tabs 230, 240 are made from any suitable material that provides sufficient strength for the intended application yet allows the locking base features 218, 219 and/or locking tab features 235, 245 to flex for engagement with each other. Preferred materials for the base 210 and tabs 230, 240 include polypropylene, acrylonitrile butadiene styrene, polycarbonate, polyethylene, and mixtures and copolymers thereof.

The stem 250 includes a tubular bottom portion 251 which comprises a cylindrical side wall, a top end 252 and a bottom end 253; and a positioning member 254 at the top end 252 of the tubular bottom portion 251. The positioning member 254 includes an opening that is coaxial with the tubular bottom portion 251. Optionally, at least one retention window 255 is located within the cylindrical side wall of the bottom portion 251. The stem 250 is made from any suitable material such as, for example, metallic materials such as stainless steel, copper, nitinol, or brass; and polymeric materials such as polypropylene, acrylonitrile butadiene styrene, polycarbonate, polyethylene, and mixtures and copolymers thereof. It is generally preferred, however, that the stem 250 comprise a metallic material.

The operation of the medical device 200 is now described with reference to FIGS. 1 to 3. A distal end of a tube 500 to be retained (e.g., a gastrostomy feeding tube) is positioned to a desired location within the body (e.g., the stomach) such that the proximal end extends from the exterior of the body (e.g., through a stoma site). A hemostat is then clipped to the tube, which is thereafter cut to a suitable length to thereby leave a short stub in which the stem 250 is inserted. The stem 250 is inserted into the proximal end 501 of the tube 500 such that the bottom portion 251 is substantially surrounded by the inner circumference of the tube 500. The outer diameter of the bottom portion 251 is preferably about the same or greater size than the inner diameter of the tube 500, thus ensuring a tight fit between the two. The positioning member 254 remains outside of the tube and is preferably placed against the proximal end of the tube when in use.

The opening 215 in the base 210 is configured to receive the tube 500 with the stem 250 therein. As shown in FIG. 1, the opening 215 in the lower surface 212 of the base 210 preferably has a shape that reflects the shape of the positioning member 254. The base 210 is placed over the tube such that the stem 250 passes through the opening 215 and extends beyond the upper surface 211 of the base 210. The base 210 is then rotated so that, when released, the positioning member 254 will rest against the upper surface 211 of the base 210. In the embodiment shown in FIG. 1, the base 210 is rotated 90° such that the positioning member 254 rests in alignment recesses 220 in the upper surface 211 of the base 210. The alignment recesses 220 serve the addition function of aligning retention windows 255, if present, with the window locking members 238, 248 on the first and second tabs 230, 240, respectively.

After the tube is inserted through the base 210 and the positioning member 254 of the stem 250 is resting against the upper surface 211 of the base 210, the first and second tabs 230, 240 are moved within first and second cavities 216, 217, respectively, towards the opening 215 in the base 210 such that the locking tab features 235, 245 engage with the locking base features 218, 219, respectively. When fully inserted, the first and second tabs 230, 240 hold the tube 500 by compression with the tube compression members 236, 246 and, preferably, with the window locking members 238, 248. As shown in cross-section in FIG. 2, the window locking members 238, 248 force the tube 500 into the retention windows 255 when the first and second tabs 230, 240 are fully inserted into the first and second cavities 216, 217. When deployed, the device rests against a patients skin 280, as shown in FIG. 2.

Figure 2:
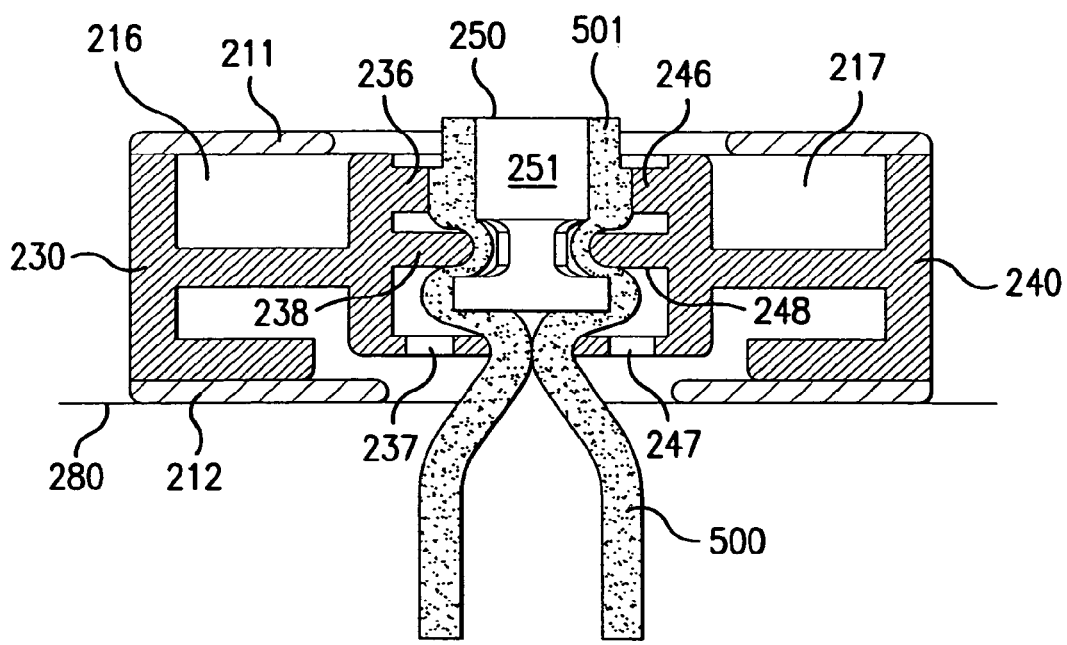
FIG. 2 shows a cross-sectional view of an embodiment of the present invention when in use.

When tube closing members 237, 247 are included in first and second tabs 230, 240, they form a "valve" by substantially closing or pinching off the tube 500, as shown in FIG. 2. One of the effects of this valve is to prevent the discharge of material from within the body through the tube 500. It is thus preferred that the tube closing members 237, 247 are sized such that, when the first and second tabs 230, 240 are fully inserted into first and second cavities 216, 217, the gap between the tube closing members 237, 247 is approximately equal to or less than twice the wall thickness of the tube. The formation of this internal valve represents a significant enhancement over conventional retention systems, in which external valves add to the complexity of such systems.

Figure 3:
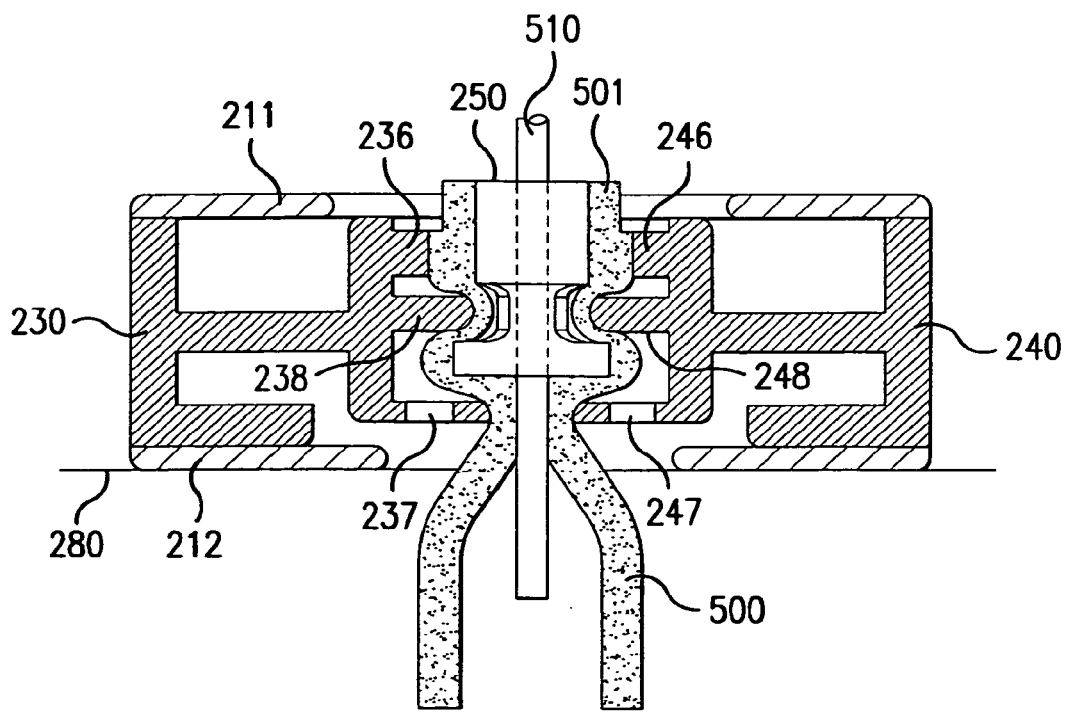
FIG. 3 shows a cross-sectional view of an embodiment of the present invention when in use with an external feeding tube inserted therethrough.

When the device 200 is used as part of a feeding system, an external feeding tube 510 is engaged with the device 200 as shown in FIG. 3. The external feeding tube 510 includes a portion that extends through the valve formed by the tube closing members 237, 247 by compressing the sides of the tube 500 against the tube closing members 237, 247, as shown in FIG. 3. The extension member is preferably made from a rigid material, such as stainless steel.

The medical device 200 preferably includes a boot 270 that fits over the base 210 and first and second tabs 230, 240 when inserted into the base 210. If used, the boot 270 rests against the patient's skin, and is thus preferably made from a soft, elastomeric material such as silicone, polyurethane or latex. If a boot is not used with the present invention, it is preferred that a pad made from a soft, elastic material such as silicone, polyurethane or latex, be placed between the patient's skin and the base 210. Such a pad optionally includes an adhesive material on one or both sides.

Figure 4:
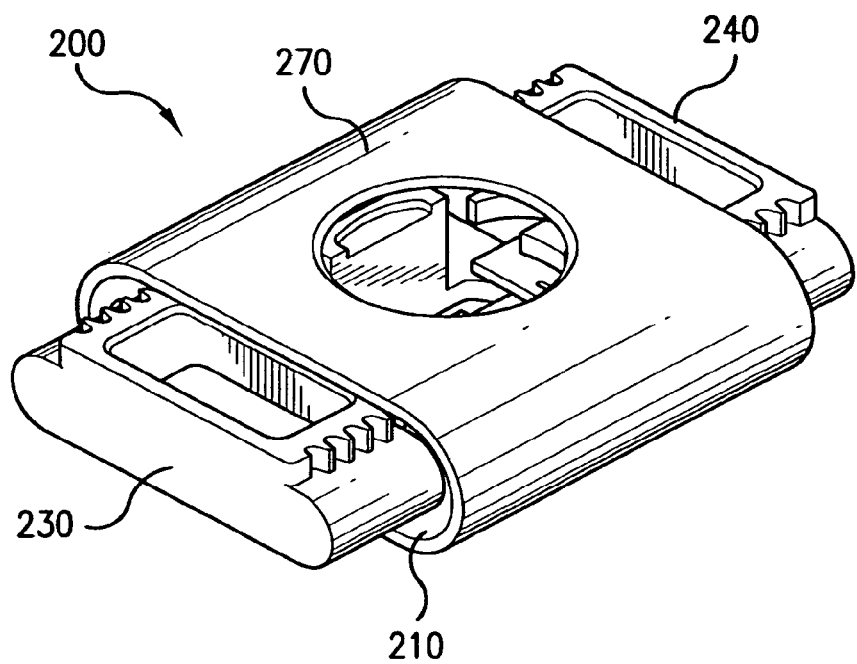
FIG. 4 shows an assembled embodiment of the present invention.
Figure 5:
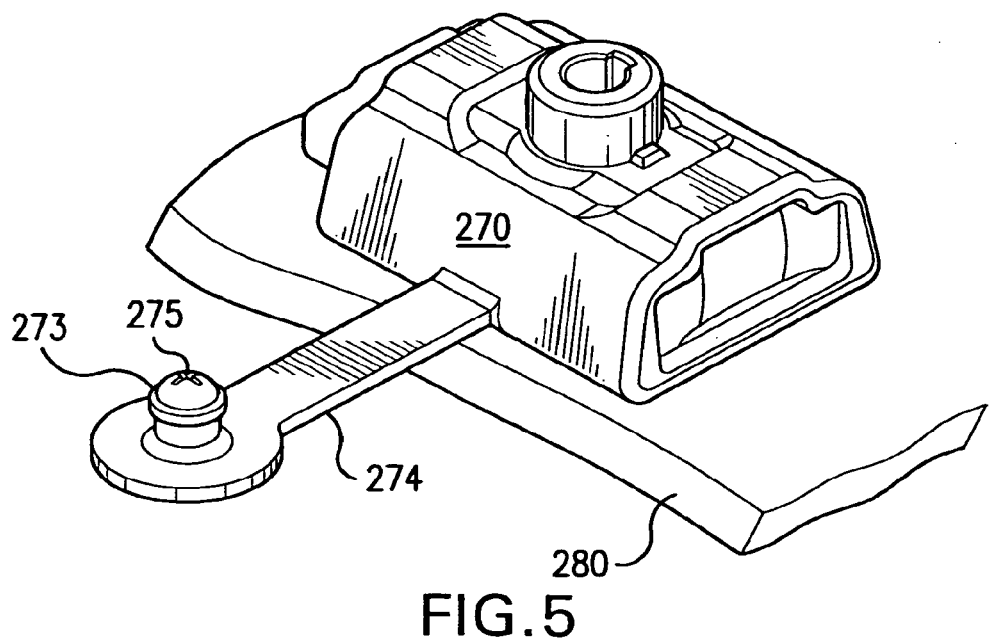
FIG. 5 shows an embodiment of the present invention that includes a boot having an attached plug.

When the boot 270 is used with the present invention, the medical device is delivered to the physician or patient as shown in FIG. 4. As such, the medical device 200 is simply positioned over the tube preferably having a stem 250 therein, the tube is positioned onto the upper surface 211 of the base 210, and the first and second tabs 230, 240 are fully inserted into the first and second cavities 216, 217, respectively, to lock the tube into the medical device 200. The boot includes upper and lower openings 271, 272 so that the tube can be inserted into the opening 215 in the base 210, and an external feeding tube can be inserted into the stem 250 for feeding the patient. The boot optionally includes a plug 273 attached to the boot 270 by an arm member 274 as shown in FIG. 5. The plug 273 is insertable into the end of the tube to prevent the flow of bodily fluids therefrom. In one embodiment, the plug 273 acts like a cap that closes the stem lumen when not in use. In another embodiment, the plug 273 includes a slit 275 that acts like a valve that can be opened by the insertion of a feeding tube.

Figure 6:
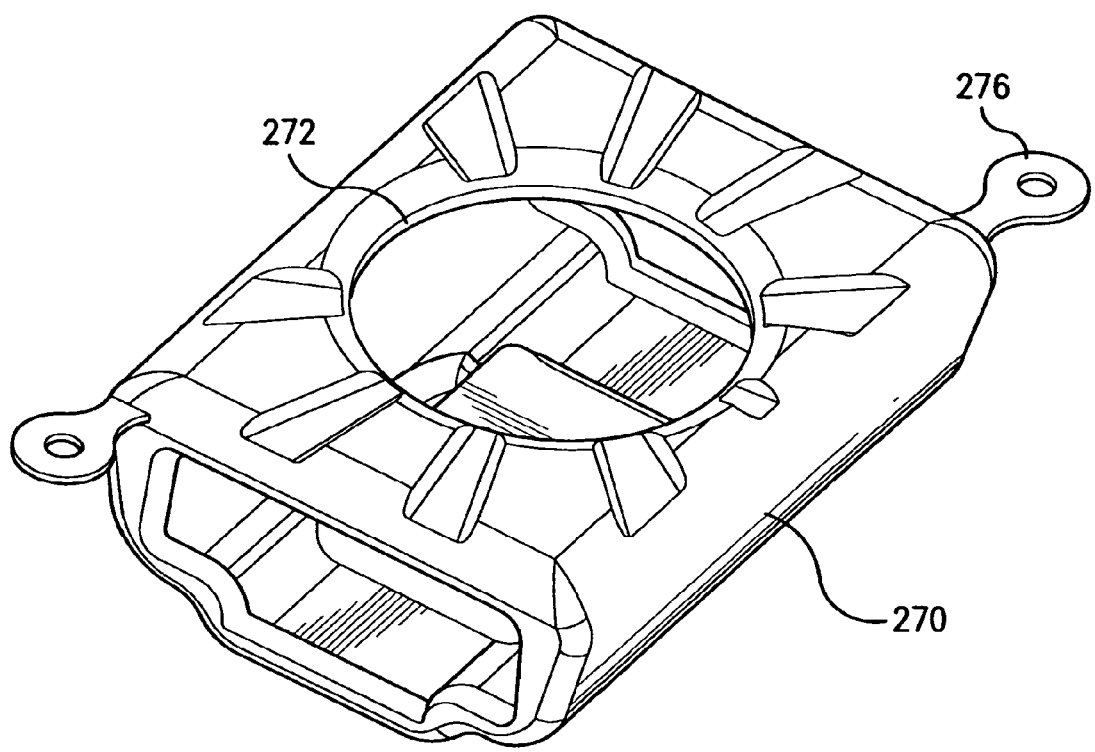
FIG. 6 shows a patterned boot, for use with an embodiment of the present invention.

The bottom surface of the boot (i.e., the surface that comes into contact with the patient's skin) is preferably patterned with recesses, grooves, or the like (FIG. 6) to minimize the contact area between the boot and the patient. The boot also optionally includes flap(s) or ear(s) 276 extending outward from the bottom surface, as shown in FIG. 6 Such flaps 276 are attached to the boot 270 or are formed as an integral part thereof, and are positioned on the bottom surface of the boot 270 at any suitable location, such as the corners as shown in FIG. 6. Preferably, the boot 270 is formed with a flap 276 at each corner of its bottom surface. The flaps 276 are used to secure (e.g., by suture) the boot 270 to the patient's skin, thereby holding the medical device 200 in place during use.

Figure 7:
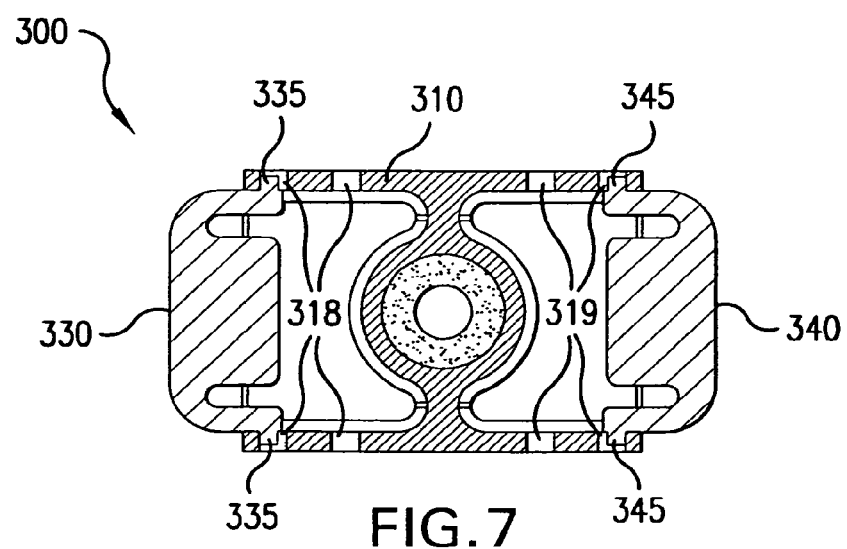
FIG. 7 shows a top view of an embodiment of the present invention in which two tabs are used.

The present invention includes several embodiments that are variations of the embodiment shown in FIG. 1. For example, the device 300 shown in FIG. 7 (top view) includes a base member 310 having base locking members 318, 319 that are positioned on the sides of the base member 310. Although the base locking members 318, 319 are shown in FIG. 7 to extend through the base member 310, the base locking members 318, 319 may simply comprise notches on the inner surface of the base member 310. Correspondingly, the first and second tabs 330, 340 each have at least one locking tab feature 335, 345 that is (are) engagable with respective locking base features 318, 319, as shown in FIG. 7. For example, the locking tab features 335, 345 snap into the respective locking base features 318, 319 when the tabs 330, 340 are advanced to a working configuration. Although not shown in FIG. 7, the tabs 330, 340 further comprise tube compression members and window locking members, and preferably include tube closing members, as shown for tabs 230, 240 in FIG. 1.

Figure 8:
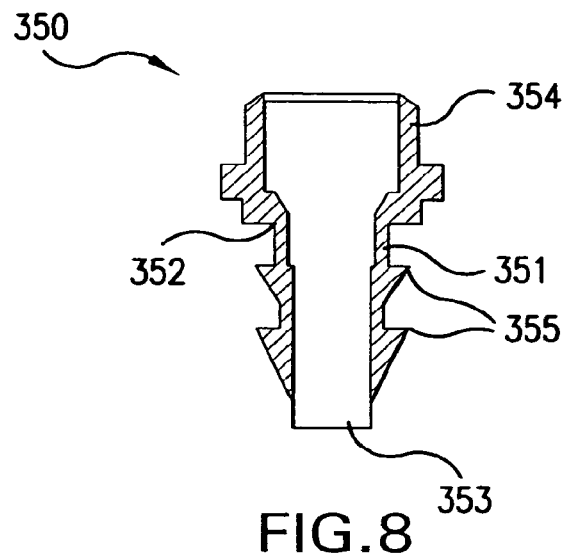
FIG. 8 shows a stem with a mechanical surface thereon, in accordance with an embodiment of the present invention.

In another embodiment, the present invention includes a stem 350, a section of which is shown in FIG. 8, rather than the stem 250. Like the stem 250, the stem 350 is designed to be inserted into the end of a tube to be retained. The stem 350 includes a tubular bottom portion 351 which comprises a cylindrical side wall, a top end 352 and a bottom end 353; and a positioning member 354 at the top end 352 of said tubular bottom portion 351. The positioning member 354 includes an opening that is coaxial with the tubular bottom portion 351. The outer diameter of the bottom portion 351 is preferably about the same or greater size than the inner diameter of a tube to be retained. The stem 350 further includes a mechanical surface 355, such as a threaded or patterned surface, to assist in gripping and holding a retained tube (as compared to the window 255 of the stem 250). When stem 350 is used in the present invention, first and second tabs 230, 240 do not include window locking members 238, 248.

Figure 9:
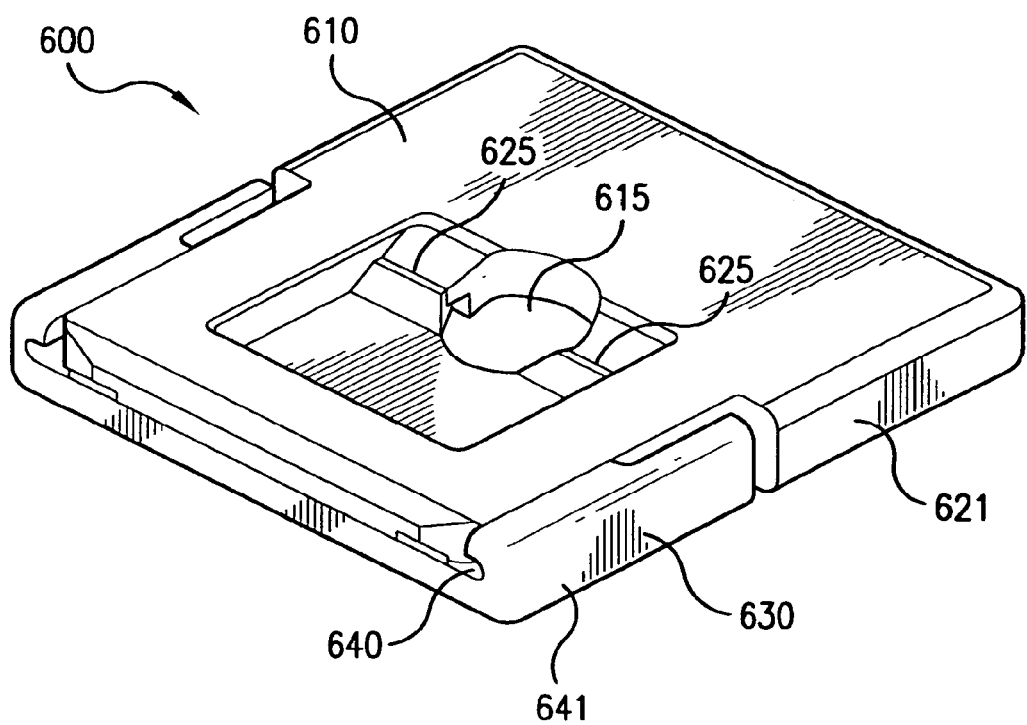
FIG. 9 shows a perspective view of an embodiment of the present invention in which the base and tab portions are substantially mirror images of each other.
Figure 10A:
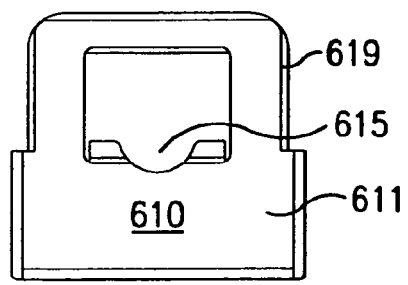
FIGS. 10A and 10B show top and bottom views, respectively, of the base of an embodiment of the present invention.

FIG. 9 shows an embodiment of the present invention in which the medical device includes only one tab. In this embodiment, the medical device 600 includes a base 610 and a first tab 630 that are substantially mirror images of each other. The base 610, shown in FIGS. 10A (top view) and 10B (bottom view) includes an upper surface 611 and a lower surface 612, which define an opening 615 for receiving a tube. The upper and lower surfaces 611, 612 further define a first side cavity 616 extending from the lower surface 612 of the base 610 and between the side walls 621. The base 610 includes a plurality of locking base teeth 618 in the lower surface 612.

Figure 10B:
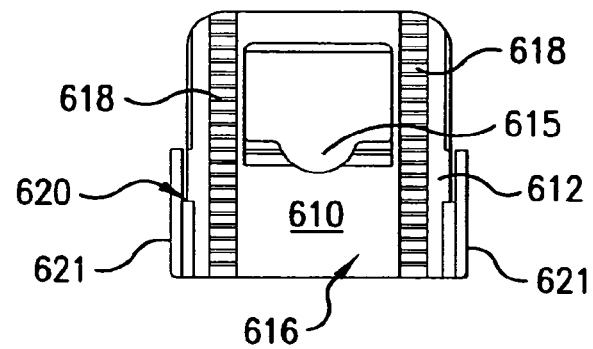

The medical device 600 includes a first tab 630 that is substantially identical to the base 610. The first tab 630 is movable within the first side cavity 616 in the base 610. The first tab 630 includes a plurality of locking tab teeth that are substantially identical to the plurality of locking base teeth 618 as shown in FIG. 10B. The locking tab teeth are engagable with the locking base teeth when the first tab 630 is moved within the first side cavity 616. Both the base 610 and the first tab 630 preferably include at least one longitudinally extending ridge (shown as 619 for the base) that is engagable with respective corresponding grooves 620, 640 in respective side walls 621, 641.

A tube to be retained by the medical device 600 is inserted through the opening 615 after the first tab 630 has been partially inserted into the first side cavity 616 of the base 610. To complete retention, the first tab 630 is fully inserted into the first side cavity 616 of the base 610, to thereby exert a compressive force on a tube within the opening 615. The first tab 630 is held in position by the engagement of the locking tab teeth with the locking base teeth. In one embodiment, the tube to be retained has a stem inserted therein to help facilitate tube retention, as previously described for stems 250 and 350. In another embodiment, the tube to be retained is held and pinched by the relative movement of the base 610 and the tab 630. In this embodiment, the tube to be retained preferably has a diameter larger than that of the opening 615 such that when the first tab 630 is fully inserted into the base 610, it is pinched at intersections 625 on either side of the opening 615. As such, when the first tab 630 is fully inserted into the base 610, a valve is formed to thereby substantially close the tube within the opening 615.

Figure 11:
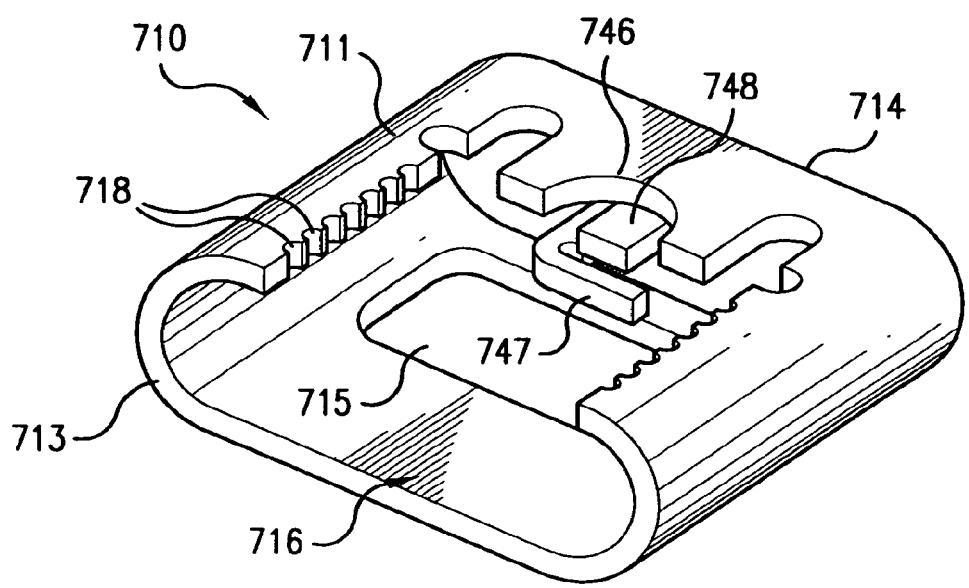
FIG. 11 shows a perspective view of the base of an embodiment of the present invention in which one tab is used.

Another embodiment 700 of the present invention which makes use of a single tab is shown in FIG. 11. This embodiment includes a base 710 having an upper surface 711, a lower surface 712, a proximal end 713 and a distal end 714. The upper and lower surfaces 711, 712 define an opening 715 for receiving a tube. The upper and lower surfaces 711, 712 further define a first side cavity 716 extending from the opening 715 to the proximal end 713. The base 710 includes a plurality of first locking base features 718 in the upper surface 711 between the opening 715 and the proximal end 713. The base 710 also includes many of the features which would otherwise be present in a second tab, if used. For example, base 710 includes a tube compression member 746 and a window locking member 748 extending from its distal end 714. The base 710 optionally includes a tube closing members 747, also extending from its distal end 714.

Figure 12:
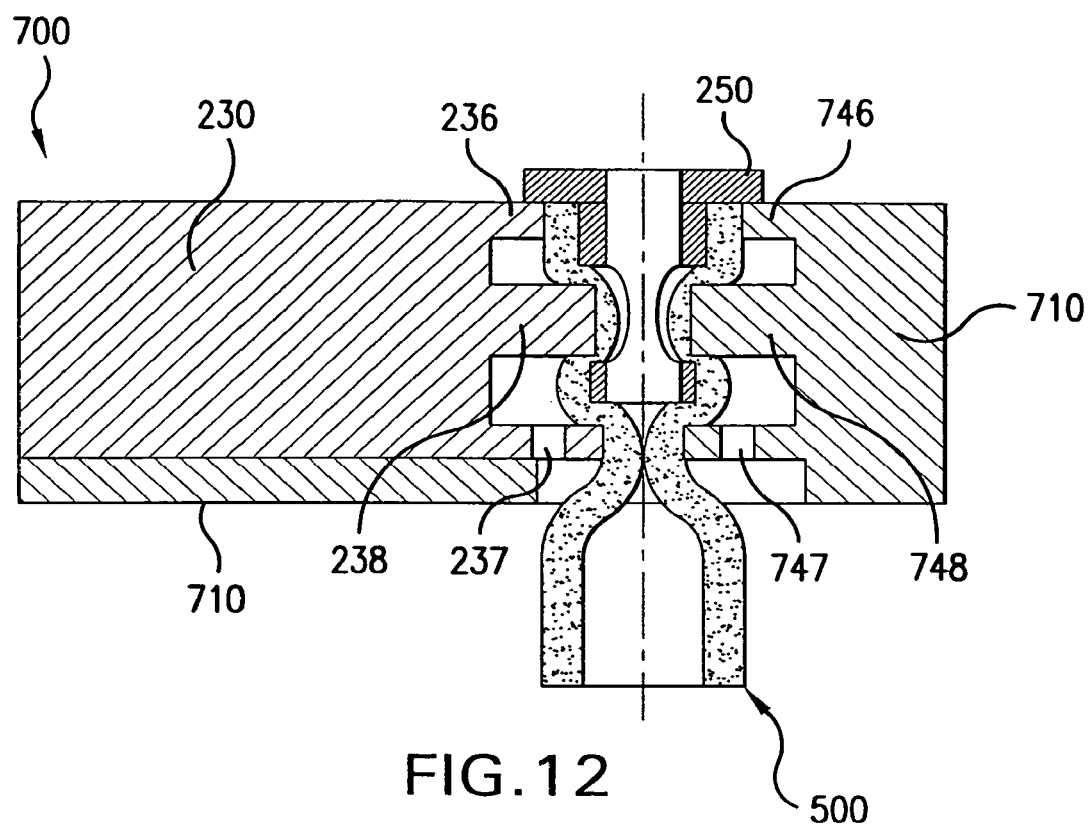
FIG. 12 shows a cross-sectional view of a single-tab embodiment of the present invention, when in use.

The medical device 700 includes a first tab, such as that shown as 230 in FIG. 1. Tube retention is accomplished in the same manner as described for the medical device 200, with the exception that a second tab is not used. A cross-section of the device 700 is shown in FIG. 12, wherein the first tab 230 is inserted into the first side cavity 716 and the device 700 is used to retain a tube 500.

Figure 13:
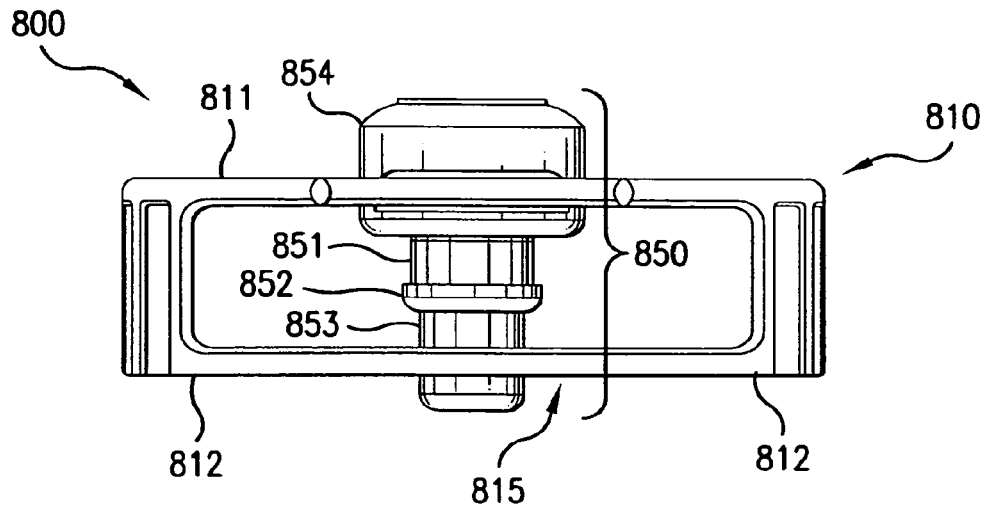
FIG. 13 shows a side view of an embodiment of the present invention in which a stem is attached to the base.

Another embodiment of the present invention in which a stem is attached to the base is shown in FIG. 13. In this embodiment 800, the base 810 includes an upper surface 811, a lower surface 812, and a stem 850 extending from the upper surface 811 towards an opening 815 in the lower surface 812. The stem 850 is characterized by a cylindrical profile that includes, for the embodiment shown in FIG. 13, a first cylindrical portion 851 adjacent the upper surface 811, a second cylindrical portion 852 adjacent the first cylindrical portion, and a third cylindrical portion 853 adjacent the second cylindrical portion. The second cylindrical portion 852 preferably has a diameter greater than either of the first or third cylindrical portions 851, 853. The stem 850 is preferably formed as an integral part of the base 810, such as by molding. The stem 850 preferably extends from the upper surface 811 through the opening 815 in the lower surface 812. The stem 850 also preferably includes a valve housing 854 extending through the upper surface 811.

Figure 14:
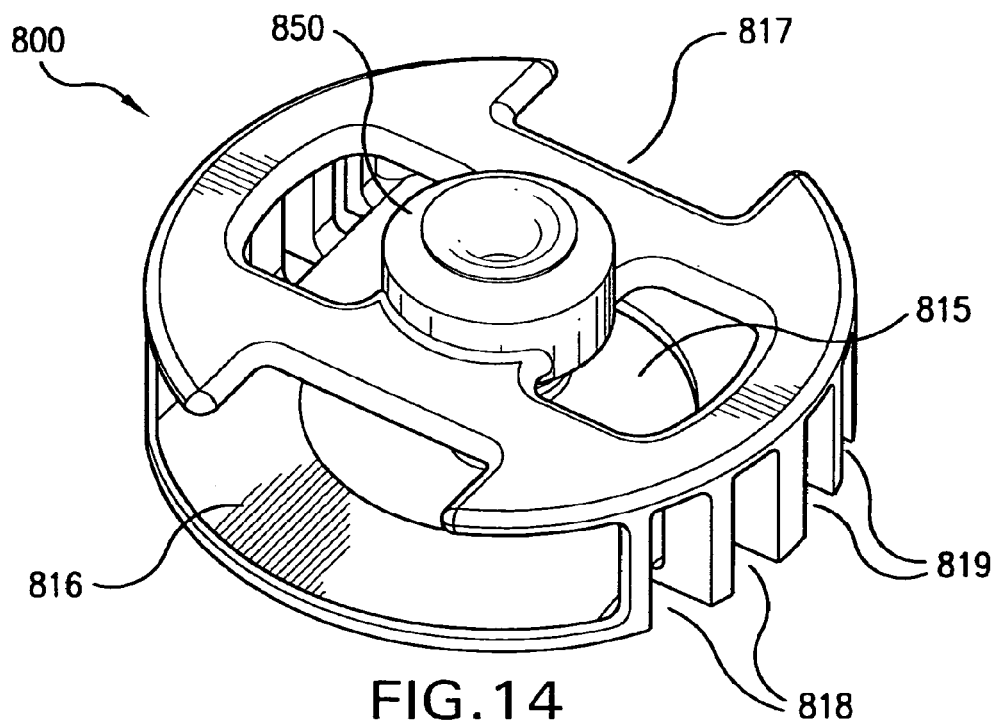
FIG. 14 shows a perspective view of an embodiment of the present invention in which a stem is attached to the base.
Figure 15:
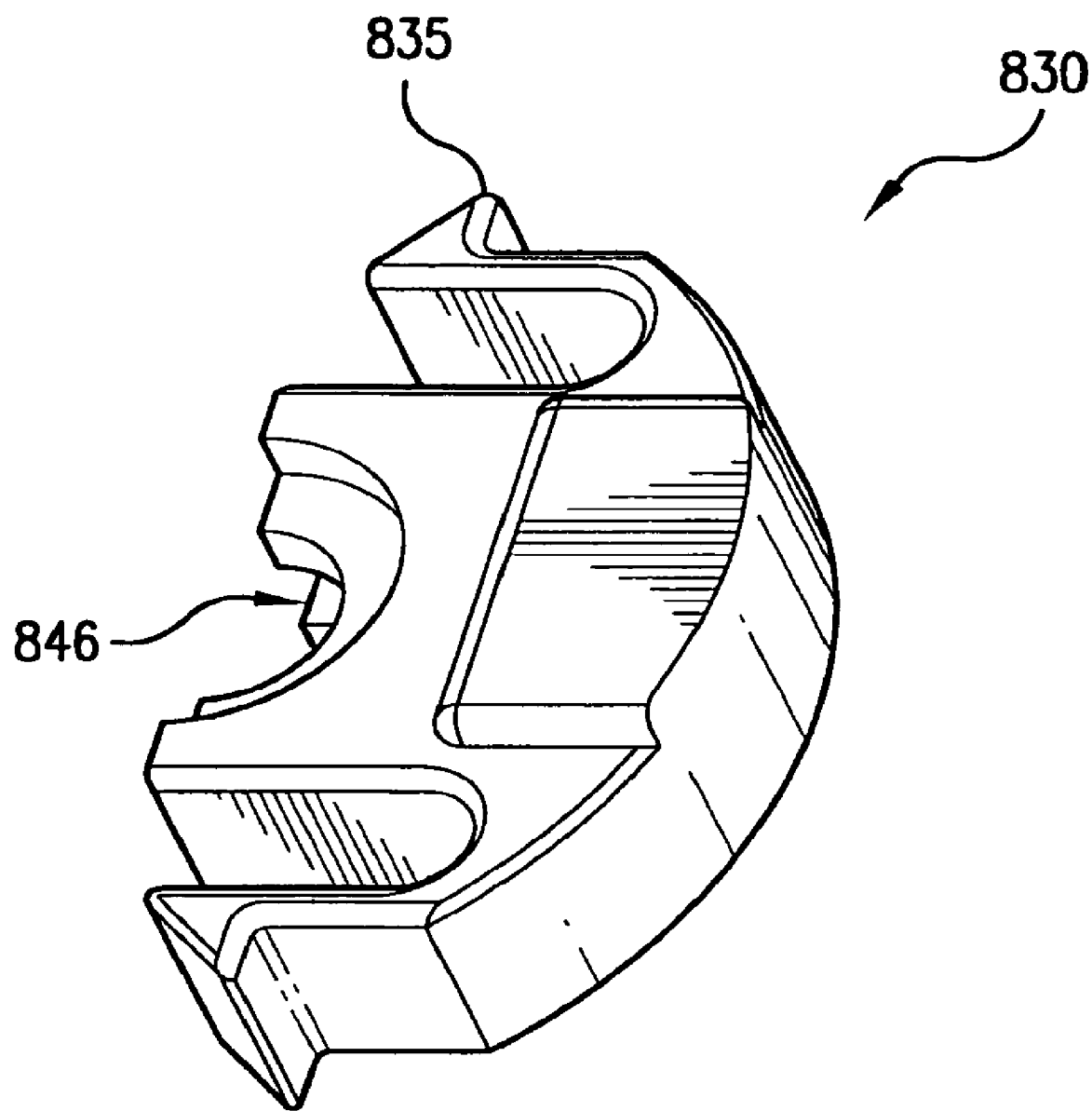
FIG. 15 shows a perspective view of a tab embodiment of the present invention.

Embodiment 800 includes a first side cavity 816, a second side cavity 817, first locking base members 818, and second locking base member 819, as shown in FIG. 14. Also included are first and second tabs that are substantially identical in structure, such as the tab 830 shown in FIG. 15, that are moveable within the first and second side cavities 816, 817. The tab 830 includes at least one locking tab feature 835 that is (are) engageable with respective locking base features 818 or 819. The tab 830 further includes a tube compression member 846 that conforms to at least part of the cylindrical profile of the stem 850.

When the device 800 is in use, a tube to be retained is placed through the opening 815 and over the stem 850. The tube preferably is placed over the stem 850 until it abuts either the upper surface 811 of the body 810 or, if used, the valve housing 854. After the tube is so positioned, the first and second tabs are moved within the first and second cavities 816, 817 such that the locking tab features, such as 835, engage with the locking base features, such as 818. When fully inserted, the first and second tabs hold the tube by compression with the tube compression members, such as 846, which conform in shape to at least part of the cylindrical profile of the stem 850.

The dimensions of the devices of the present invention are limited only by manufacturing capabilities. The devices and their respective components are made by suitable methods known to those of skill in the art, such as injection molding, casting, machining, and the like. The devices are sized to fit, for example, feeding tubes of size #5 to #24 French, but can be sized for any other tube sizes by appropriate sizes of the base, tab(s) and stem.

The present invention provides for the low profile retention of flexible tubes that extend from the body as a result of any one of a number of medical procedures. The medical devices of the present invention are easy to use, provide a high retention strength, and provide a reliable valve and feeding system interface. Although the present invention has been described with respect to several exemplary embodiments, there are many other variations of the above-described embodiments which will be apparent to those skilled in the art, even where elements have not explicitly been designated as exemplary. It is understood that these modifications are within the teaching of the present invention, which is to be limited only by the claims appended hereto.

What is claimed is:

1. A method for retaining a proximal end of a tube outside of the body of a patient, wherein a distal end of the tube is inserted into the body of the patient, the method comprising:
   providing a base having an opening for receiving the proximal end of said tube, said base comprising a first locking base feature;
   providing a first tab movable with respect to said base, said first tab comprising a first locking tab feature, said first locking tab feature being engageable with said first locking base feature;
   providing a stem, wherein the stem comprises:
      a tubular bottom portion insertable into the proximal end of said tube, said tubular bottom portion comprising a cylindrical side wall, a top end and a bottom end; and
      a positioning member at the top end of said tubular bottom portion, said positioning member defining an opening coaxial with said tubular bottom portion;
   inserting the proximal end of the tube into the opening of the base; and
   moving the first tab relative to the base, wherein said first locking tab feature engages with said first locking base feature, and wherein the movement and engagement results in compressing the proximal end of the tube.

2. The method of claim 1, wherein:
   said first locking base feature comprises a first plurality of teeth on said base; and
   said plurality of teeth on said base are engagable with said first locking tab feature.

3. The method of claim 1, wherein:
   said first locking tab feature comprises a plurality of teeth on said first tab; and
   said plurality of teeth on said first tab are engagable with said first locking base feature.

4. The method of claim 1, wherein said first locking base feature comprises a locking opening in said base;
   said first locking tab feature comprises a locking member extending from said first tab; and
   said locking member is engageable with said locking opening.

5. The method of claim 1, wherein when said first locking tab feature is engaged with said first locking base feature, a first tube compression member comes into contact with said tube.

6. The method of claim 1, wherein said first tab includes a first tube closing member extending from a distal end of said first tab, and when said first locking tab feature is engaged with said first locking base feature, said first tube closing member extends into said opening in said base.

7. The method of claim 1, further comprising a second tab movable with respect to said base, said second tab comprising a second locking tab feature, said second locking tab feature being engageable with a second locking base feature.

8. The method of claim 1, further comprising a boot placed around said base, said boot comprising:
   an upper surface juxtaposed against an upper surface of said base;
   a lower surface juxtaposed against a lower surface of said base; and a first opening in said upper surface of said boot and a second opening in said lower surface of said boot, said first and second openings of said boot being in axial alignment with said opening in said base.

9. The method of claim 1, further comprising the steps of:
inserting the tubular bottom portion of the stem into the proximal end of the tube; and
positioning said positioning member against an upper surface of said base.

10. The method of claim 1, wherein:
said base includes an alignment recess in said upper surface of said base; and
said positioning step includes positioning said positioning member within said alignment recess.

11. A method for retaining a proximal end of a tube outside of the body of a patient, wherein a distal end of the tube is inserted into the body of the patient, the method comprising:
  (i) providing a medical device for retaining the proximal end of the tube, comprising:
    (a) a base comprising an upper surface and a lower surface, wherein an opening extends through said lower surface, said opening for receiving said tube, and wherein said upper and lower surfaces define a first side cavity between said upper and lower surfaces;
    (b) a first tab having at least a portion that is movable within said first side cavity, said first tab comprising an upper surface, a lower surface, a proximal end and a distal end, and a first tube compression member extending from the distal end of said first tab; and
    (c) a stem comprising a tubular element insertable into the proximal end of said tube;
  (ii) inserting the tubular element into the proximal end of said tube and positioning the proximal end of the tube within the opening in the base; and
  (iii) moving the first tab relative to the base, wherein the movement results in compressing the proximal end of the tube.

12. The method of claim 11, wherein said base comprises a first locking base feature and said first tab comprises a first locking tab feature, and where moving the first tab relative to the base results in said first locking tab feature engaging with said first locking base feature.

13. The method of claim 12, wherein when said first locking tab feature is engaged with said first locking base feature, a first tube compression member comes into contact with said tube.

14. The method of claim 12, further comprising a second tab movable with respect to said base, said second tab comprising a second locking tab feature, said second locking tab feature being engageable with a second locking base feature.

15. The method of claim 11 wherein the stem is separate from the base.

16. The method of claim 11 wherein the stem is part of the base.

17. A method for retaining a proximal end of a tube outside of the body of a patient, wherein a distal end of the tube is inserted into the body of the patient, the method comprising:
  (i) providing a medical device for retaining the proximal end of the tube, comprising:
    (a) a base comprising an upper surface, a lower surface, and an opening for receiving said tube, said base comprising a first locking base feature;
    (b) a stem comprising a bottom portion insertable into the proximal end of said tube, wherein when said medical device is in an assembled configuration, said bottom portion of said stem is placed into the end of said tube, said tube is placed into said opening in said base, and said bottom portion of said stem projects toward said lower surface of said base; and
    (c) a first tab movable with respect to said base for compressing the tube, said first tab comprising a first locking tab feature;
  (ii) inserting the bottom portion of the stem into the proximal end of said tube and positioning the proximal end of the tube within the opening in the base; and
  (iii) moving the first tab relative to the base, wherein the movement results in said first locking tab feature engaging with said first locking base feature to hold the first tab in a fixed position with respect to the base.

18. The method device of claim 17, wherein said first tab comprises a first tube compression member, and when said first locking tab feature is engaged with said first locking base feature, said first tube compression member comes into contact with said tube.

* * * * *